United States Patent
Mathisen

(10) Patent No.: US 10,188,622 B2
(45) Date of Patent: *Jan. 29, 2019

(54) USE OF A COMPOSITION COMPRISING FISH OIL AND JUICE FOR THE TREATMENT AND/OR POST TREATMENT OF CANCER

(71) Applicant: Smartfish AS, Oslo (NO)

(72) Inventor: Janne Sande Mathisen, Oslo (NO)

(73) Assignee: Smartfish AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/850,763

(22) Filed: Dec. 21, 2017

(65) Prior Publication Data

US 2018/0110749 A1  Apr. 26, 2018

Related U.S. Application Data

(63) Continuation of application No. 14/786,499, filed as application No. PCT/NO2014/050061 on Apr. 22, 2014, now Pat. No. 9,877,944.

(30) Foreign Application Priority Data

Apr. 22, 2013 (NO) .................................. 20130552

(51) Int. Cl.
| | | |
|---|---|---|
| A61K 31/20 | (2006.01) |
| A61K 31/202 | (2006.01) |
| A61K 35/60 | (2006.01) |
| A61K 36/00 | (2006.01) |
| A61K 9/00 | (2006.01) |
| A61K 9/107 | (2006.01) |
| A61K 47/36 | (2006.01) |
| A23L 33/105 | (2016.01) |
| A23L 33/115 | (2016.01) |

(52) U.S. Cl.
CPC .......... *A61K 31/202* (2013.01); *A23L 33/105* (2016.08); *A23L 33/115* (2016.08); *A61K 9/0095* (2013.01); *A61K 9/107* (2013.01); *A61K 35/60* (2013.01); *A61K 36/00* (2013.01); *A61K 47/36* (2013.01); *A23V 2002/00* (2013.01)

(58) Field of Classification Search
CPC ...... A61K 31/202; A61K 47/36; A61K 36/00; A61K 9/0095; A61K 9/107; A61K 35/60; A23L 33/115; A23L 33/105; A23V 2002/00
USPC ........................................................ 514/560
See application file for complete search history.

(56) References Cited

U.S. PATENT DOCUMENTS

| | | |
|---|---|---|
| 7,179,491 B1 | 2/2007 | Mag |
| 2002/0012710 A1 | 1/2002 | Lansky |

(Continued)

FOREIGN PATENT DOCUMENTS

| | | |
|---|---|---|
| EP | 0713653 A1 | 5/1996 |
| WO | 2004/075647 A1 | 9/2004 |

(Continued)

OTHER PUBLICATIONS

Istfan et al, 1 alpha,25-dihydroxyvitamin D and fish oil synergistically inhibit G1/S-phase transition in prostate caner cells, Journal of Steroid Biochemistry & Molecular Biology, 103, 2007, p. 726-730 (Year: 2007).*

(Continued)

*Primary Examiner* — Taylor V Oh

(74) *Attorney, Agent, or Firm* — Venable LLP

(57) ABSTRACT

Disclosed is a composition including a fish oil and a juice in an oil-in-water emulsion for use in treatment and post-treatment of cancer.

15 Claims, 6 Drawing Sheets

(56) References Cited

U.S. PATENT DOCUMENTS

2009/0202679 A1    8/2009  Mathisen
2011/0135745 A1    6/2011  Mathisen et al.

FOREIGN PATENT DOCUMENTS

WO    2006/120120 A1    11/2006
WO    2007/064222 A1     6/2007
WO    2009/120091 A1    10/2009

OTHER PUBLICATIONS

International Preliminary Report on Patentability for International Application No. PCT/NO2014/050061, dated Jun. 1, 2015.
Norwegian Search Report dated Nov. 18, 2013 for Norwegian Application No. 20130552.
Nutrifriend 1100 publication, Smartfish, 3 captures Feb. 19, 2012-Oct. 15, 2012 (2 pages).
Ueda et al., "Effect of oil-in-water lipid emulsions prepared with fish oil or soybean oil on the growth of MCF-7 cells and HepG2 cells," Journal of Pharmacy and Pharmacology, 60 (Apr. 22, 2008) pp. 1069-1075.
Tang et al., "Concomitant supplementation of lycopene and eicosapentaenoic acid inhibits the proliferation of human colon cancer cells," Journal of Nutritional Biochemistry, 20 (2009) pp. 426-434.
Taneja et al, "Challenges for the Delivery of Long-Chain n-3 Fatty Acids in Functional Foods," Annual Review of Food Science Technology 3 (2012), pp. 105-123.

\* cited by examiner

USE OF A COMPOSITION COMPRISING FISH OIL AND JUICE FOR THE TREATMENT AND/OR POST TREATMENT OF CANCER

This application is a continuation of U.S. application Ser. No. 14/786,499, filed Oct. 22, 2015, which is a national phase entry of PCT/NO2014/050061, filed on Apr. 22, 2014, which claims the benefit of NO 20130552, filed on Apr. 22, 2013, the contents of each of which are incorporated by reference herein in their entirety.

FIELD OF THE INVENTION

The present invention provides a composition comprising fish oil and juice in an oil-in-water emulsion for use in treatment and post-treatment of cancer.

BACKGROUND OF THE INVENTION

The potential benefits of fish oil emerged from the observation that cardiovascular diseases and cancer incidence rates are generally low in eskimos of Alaska and Greenland. These populations have a diet high in fish and low in carbohydrates which is in contrast to the diets in Europe and North America.

Fish oil is the richest dietary source of long-chain omega-3 polyunsaturated fatty acids (PUFA). Fatty acids are the building blocks of dietary fats, and are stored substantially in the form of triglycerides. The body cannot however, produce these fatty acids and must obtain them from food sources or from supplements. Three fatty acids compose the omega-3 family: alpha-linolenic acid (ALA), eicosapentaenoic acid (EPA) and docosahexanoic acid (DHA). ALA is found in e.g. walnuts, some types of beans and olive oils. EPA and DHA are found in fish, including fish oil and supplements.

The omega-3 fatty acids are essential to life at any stage, even before birth. They are essential building blocks of the membrane of every cell in the body and their presence are a necessity for maintaining an adequate cell membrane. They do also contribute in the regulation of most biological functions. There is substantial epidemiological evidence that consumption of fish or of long chain n−3 polyunsaturated PUFA, especially EPA and DHA protect against cardiovascular disease in Western populations. Long chain n−3 PUFA lower fasting plasma triacylglycerol concentrations and reduce postprandial lipaemic response. Fish oil also provides anti-inflammatory and anti-aggregatory effects which play a crucial role in the treatment of atherosclerosis and thrombosis.

Even though convincing results have been presented where omega-3 has been employed in the treatment of different conditions, very limited data concerning omega-3 or fish oil in the treatment of cancer is available. It seems so far that the results are ambiguous.

The American Cancer Society declares however, that some promising results regarding fish oil and cancer have been presented and that these findings deserve further studies.

In one study a carcinogen-induced cancer model showed that a high intake of fish oil significantly lowered the cancer incidence in animal studies as compared to animals fed with either low fat diets or high oil corn diets (Welsch, C W. Cancer Res., 52:2040s-2048s, 1992).

In a review article by Gleissman H., et al., (Experimental Cell Research 316 (2010) 1365-1373), it is presented that conventional chemotherapeutics are considered "double-edged swords" as they kill cancer cells but also strike the healthy cells causing severe morbidity and sometimes also mortality. It is further discussed if omega-3 in this setting works as a "sword and shield", by being cytotoxic to cancer cells, and at the same time protect healthy cells from these deleterious effects.

NO 324262 discloses a composition comprising low oxidized fish oil and juice in an oil-in-water emulsion.

From research leading to the present invention it was surprisingly found that the composition comprising low oxidized fish oil and juice in an oil-in-water emulsion could be used in cancer therapy. The results which are elaborated below showed decrease in cancer cell proliferation and increase in cancer cell apoptosis, as well as a delay in tumour development following treatment with a composition of the invention comprising fish oil and juice.

SUMMARY OF THE INVENTION

The present invention encompasses a composition comprising a combination of fish oil and juice in an oil-in-water emulsion, for the use in treatment and/or post treatment of cancer, wherein said fish oil is selected from fish oil having a totox value below 20 and omega-3 content above 10% by weight based on the total weight of the fish oil and wherein a suitable emulsifier is used to stabilize the emulsion.

Preferred embodiments are set forth in the dependent claims and in the detailed description of the present invention.

DETAILED DESCRIPTION OF THE INVENTION

By the present invention it has surprisingly been found that a composition comprising fish oil and juice in an oil-in-water emulsion could be used in cancer therapy.

It has surprisingly been found that use of a composition according to the present invention was a strong inducer of cancer cell apoptosis revealing a great potential in cancer treatment.

Further, it has surprisingly been found that use of the composition according to the present invention contributed to an antiproliferative effect in cancer cell lines, also revealing a great potential in cancer treatment.

A further study in an animal model surprisingly revealed a delay in tumor development in mice receiving the composition according to the invention.

Thus, it is an object of the present invention to provide a composition comprising fish oil and juice for use in treatment and/or post-treatment of cancer.

Different aspects of compositions comprising fish oil and juice are described in the Norwegian Patent NO 324262, although further modifications of the composition may be employed in the present invention.

The compositions of the present invention has been shown to have high stability as marine emulsion and enables low oxidation and keeps the vulnerable nutrients intact and potent which in turn results in increased absorption and high bioavailability.

Figure 5:
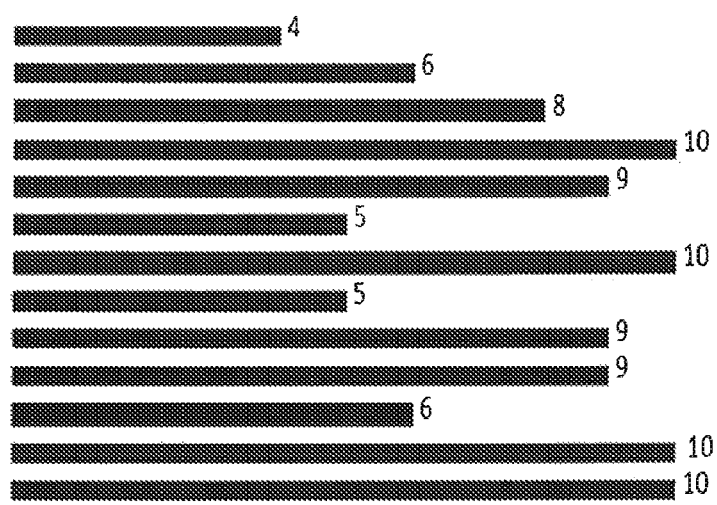
FIG. 5. Illustrates the results of a test among 13 cancer patients wherein the tastefulness of a composition of the invention (Nutrifriend 1100) was tested. The taste was scored from 1 to 10 (wherein 10 were the highest score and the best taste). 7 patients gave the composition a score of 9-10, 3 patients scored the composition to 6-8, and 3 patients scored the composition to 4-5.

Fish oil in a composition often contributes to an unwanted taste and after taste of fish. The composition for use in the present invention has the advantage of being tasteful which is an important prerequisite when treating cancer patients experiencing changes in taste and loss of appetite. The test illustrated in FIG. 5 underline the fact that the composition was perceived as being tasteful by hospitalized cancer patients. In said test 13 cancer patients tested the composition with regard to tastefulness. The taste was scored from 1 to 10 (wherein 10 were the highest score and the best taste). 7 patients gave the composition a score of 9-10, 3 patients scored the composition of 6-8, and 3 patients scored the composition of 4-5.

It has now surprisingly been found that the composition disclosed in NO 324262 can be used for the treatment and post treatment of cancer.

One aspect of the present invention relates to a composition comprising a combination of fish oil and juice in an oil-in-water emulsion, for the use in treatment and/or post treatment of cancer, wherein said fish oil is selected from fish oil having a totox value below 20 and omega-3 content above 10% by weight based on the total weight of the fish oil and wherein a suitable emulsifier is used to stabilize the emulsion.

The fish oil may be selected from any fish oil preparation of appropriate quality, i.e. the level of oxidation should be low. To be of appropriate quality the level of oxidation given as the totox-value (2 times the peroxide value (PV) added with the anisidine value (AV)) should be below 20, preferably below 10. Such fish oils of appropriate quality are usually clear oils with a very mild fishy odour and taste.

The content of omega-3 fatty acids differs widely in different fish oil preparations. It is preferable that the content of omega-3 is high. According to preferred embodiments, the content of omega-3 fatty acids in the fish oil used in the composition of the invention should be at least 10%, preferably at least 16%, or most preferably above 30% by weight based on the weight of the fish oil.

One preferred embodiment of the present invention provides a composition wherein the content of the fish oil is about 0.5%-15% by weight based on the total weight of the composition, more preferably in the range of 2%-7%, most preferably about 2%-5%.

In further embodiments of the present invention the content of the juice is about 30-95% by weight based on the total weight of the composition. The use may be selected from fruit and/or berries having a suitable high level of antioxidants. It is further preferred that the fruit possess a minimum level of metal ions functioning as oxidizing agent.

Preferred juices may be selected from the following group:

pomegranate, apricot, grapefruit, orange, cranberry, rosehip, pineapple, black chokeberry, mulberry, cloudberry, acerola, raspberry, watermelon, peach, grapes, cherry, jambolao, apple, mango, pear, aronia, passion fruit and kiwi. Further, the juice may be selected from beetroot, carrot, lingonberry (cowberry), guava, blackberry or greens like kale, spinach, celery, parsley or cucumber. Any juice suitable for stabilizing the oxidation of the fish oil may, however, be used. The juice may be prepared by adding water to juice concentrates and juice purée obtaining a normal ready-to use juice. The juice may also be a fresh pressed juice.

To stabilize the oil-in-water emulsion comprising fish oil and juice suitable emulsifiers are be used. Suitable emulsifiers may be selected from the following group:

milk solids, whey protein, oat protein and pea protein. The emulsifier may be e.g. Grindsted or Lacprodan, but any suitable emulsifier may be employed. Further the present invention may comprise thickening agent which preferably may be pectin preferably from oat, more preferably from fruit e.g. citrus.

Further the composition according to the invention may comprise yoghurt powder, hemp milk powder, almond milk powder or oat milk powder. By adding such additives, the composition thickens giving an inviting consistency. The amount added may be in the range of 5-10% by weight based on the total weight of the composition.

In one embodiment the composition further comprises vitamin D. As an example the amount of vitamin D is from 1 µg to 2000 µg per unit dose of 200 ml, preferably from 5 µg to 50 µg per unit dose of 200 ml, most preferably 10 µg to 20 µg per unit dose of 200 ml.

Further the composition according to the invention may be added proteins which may be favourable to patients suffering from cancer and/or cancer associated adverse effects such as cachexia.

In a further preferred embodiment of the present invention the composition may comprise sweeteners, flavouring agents, antioxidants and preservatives. Preferred preservative and sweetener may be potassium sorbate and xylitol respectively.

In one embodiment the composition is free of any milk ingredients.

In one embodiment, the composition are not added any additional antioxidant not naturally present.

The composition of the invention has been shown to be useful in the treatment and post treatment of cancer. In a study, pancreatic ductal adenocarcinoma (PDAC) cells were used to investigate the potential apoptotic effect of a composition of the invention by studying the caspase-3 activity. The enzyme caspase-3 is activated in apoptotic cells, thus increased caspase-3 activity is a direct indication of increased apoptotic activity.

The caspase-3 activity was studied both in an enzyme assay and in an immunofluorescence assay.

The results of the enzyme assay indicate that the composition of the present invention induced caspase-3 expression at a level of 9.6±1.10 µM in PDAC cells co-cultured with NK cells. In comparison the levels of caspase-3 were 5.5±0.48, 6.3±0.31 and 6.1±0.48 in similar PDAC co-cultures without any stimulation, with resolvinD1 stimulation and with DHA stimulation, respectively. (Table 1)

Figure 6:
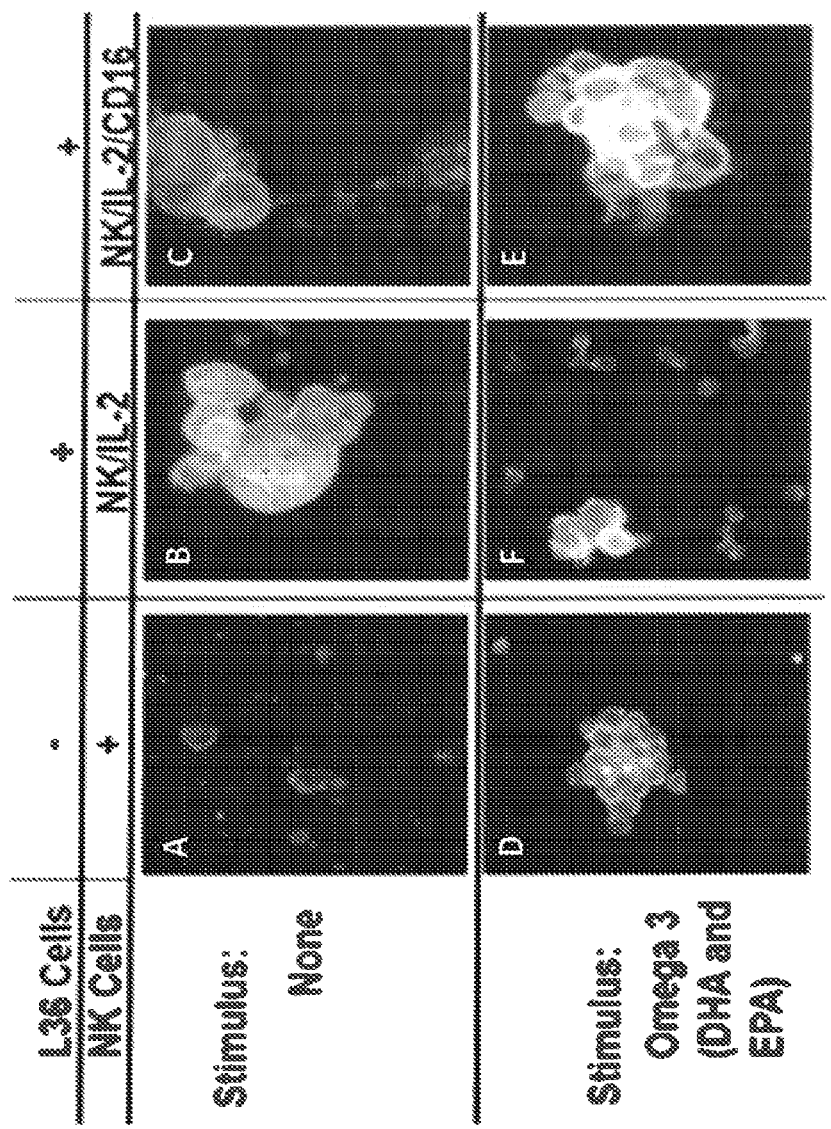
FIG. 6. Illustrates the induction of caspase-3 (red) in co cultures of L3.6 cancer cells with NK (IL-2) or NK (IL-2/CD16) cells. A composition of the invention named Smartfish Nutrifriend 2000 (identified Omega 3(DHA and EPA) in the figure was used. Without Smartfish ((B) and (C)), MP2 cells (large green cells) with NK cells (small green cells or blue nuclei with residual cytoplasm) have mostly green cytoplasm except for orange patches indicating survival. With Smartfish, ((E) and (F)), cancer cells and NK cells have mostly yellow cytoplasm indicating caspase-3 apoptosis; only few cancer cells are surviving in (E).

The results were confirmed in an immunofluorescence study showing significant effect of the composition of the invention. As shown in FIG. 6, stimulation of a co-culture of L3.6 cancer cells and NK cells stimulated with a composition of the invention showed increased apoptotic activity (FIG. 6).

Interferon-γ (IFNγ) is an important cytokine of the immune system produced a.o. by NK cells, and is known to have immunostimulatory and immunomodulatory effects. In a limited study, the levels of IFNγ were investigated in PDAC cells co-cultured with NK cells. The results showed that IFNγ was not produced by NK cells alone but by NK cells in co-culture with PDAC cells at a level of 158 pg/ml. Production of INFγ was decreased by treatment of a composition of the invention to 119 pg/ml. (Table 2)

Thus, preferred types of cancers that can be treated with the composition of the invention are pancreatic cancer in particular pancreatic ductal adenocarcinoma.

In another cell line study conducted by the inventor three human epithelial colon cancer cell lines were used to investigate the potential antiproliferative effect of the composition compared with marine oils, by measuring the effect on cell proliferation and induction of apoptosis.

Figure 1:
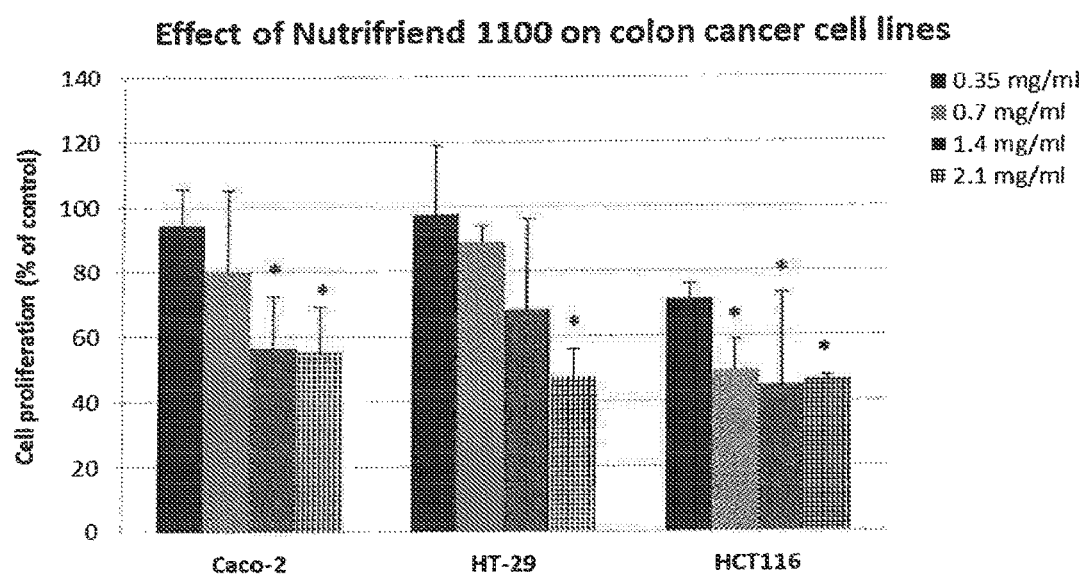
FIG. 1. Illustrates the effect of a composition of the invention (Nutrifriend 1100) on the cell proliferation of Caco-2, HT-29 and HCT116 cancer cell lines. The cells were incubated for 24 hours with increasing concentrations of the composition (Nutrifriend 1100) before the cell proliferation were measured relative to control cells (incubated with cell medium). Values are mean with standard deviation of three independent experiments. The data were analyzed with one-way ANOVA together with Tukey's multiple comparisons test, using the statistical program MINITAB 16. Significance compared to control values was established at $p \leq 0.05$ (*).
Figure 2:
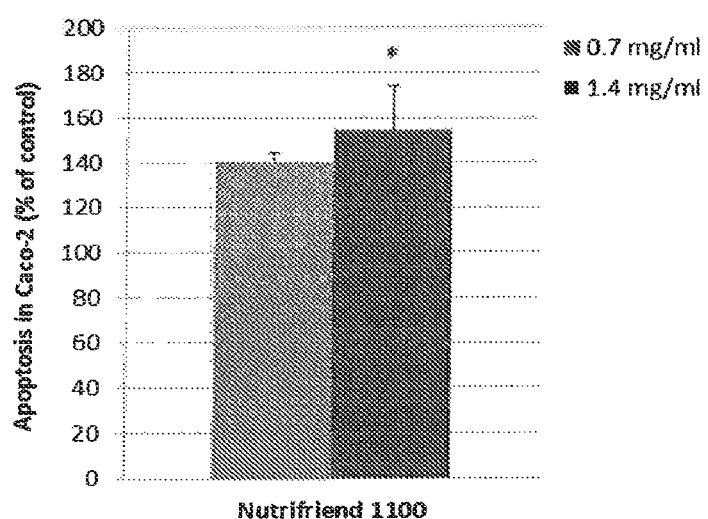
FIG. 2. Illustrates the effect of a composition of the invention (Nutrifriend 1100) on the induction of apoptosis in the Caco-2 cancer cell line. The cells were incubated for 4 hours with increasing concentrations of the composition (Nutrifriend 1100) before the apoptosis were measured relative to control cells (incubated with cell medium). Values are mean with standard deviation of two independent experiments. The data were analyzed with one-way ANOVA together with Tukey's multiple comparisons test, using the statistical program MINITAB 16. Significance compared to control values was established at $p \leq 0.05$ (*).
Figure 3:
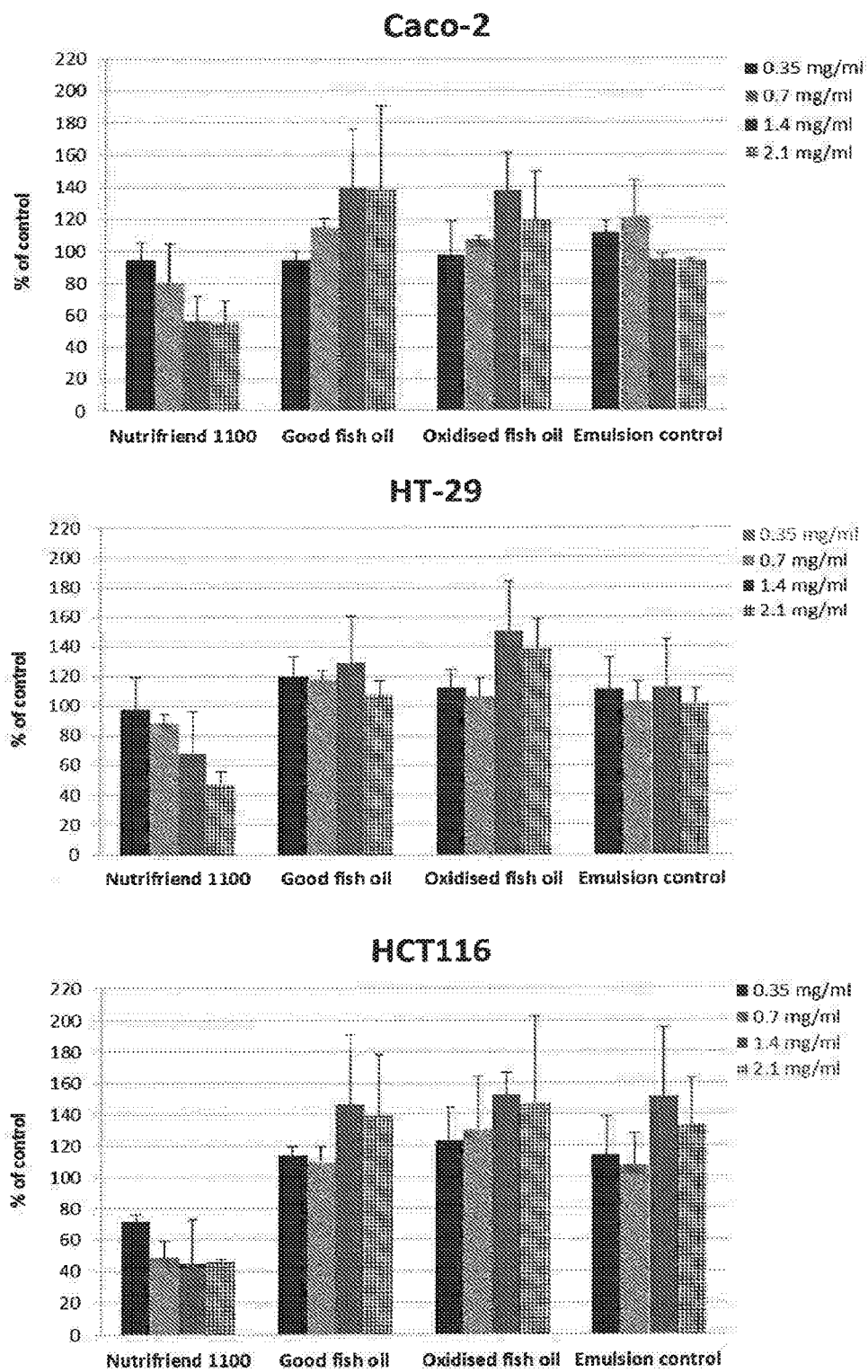
FIG. 3. Illustrates the effect of a composition of the invention (Nutrifriend 1100) and two fish oil samples, i.e. good fish oil and oxidized fish oil, on the cell proliferation of Caco-2, HT-29 and HCT116 cancer cell lines. The cells were incubated for 24 hours with increasing concentrations of samples before the cell proliferation were measured relative to control cells (incubated with cell medium). Values are mean with standard deviation of three independent experiments.

The results indicate that the composition of the present invention has an antiproliferative effect on all three cell lines (FIG. 1), and that this inhibition of cell proliferation is due to an induction of apoptosis (FIG. 2). The largest effect was seen on the HCT116 cell line, were a concentration of 0.7 mg/ml (with respect to oil content) gave a significant (about 50%) decrease in cell proliferation compared to control cells. The control fish oil samples showed no inhibition of cell proliferation (FIG. 3).

Thus, preferred types of cancers that can be treated with the composition of the invention are colorectal cancers such as colon cancer and rectal cancer.

Figure 4:
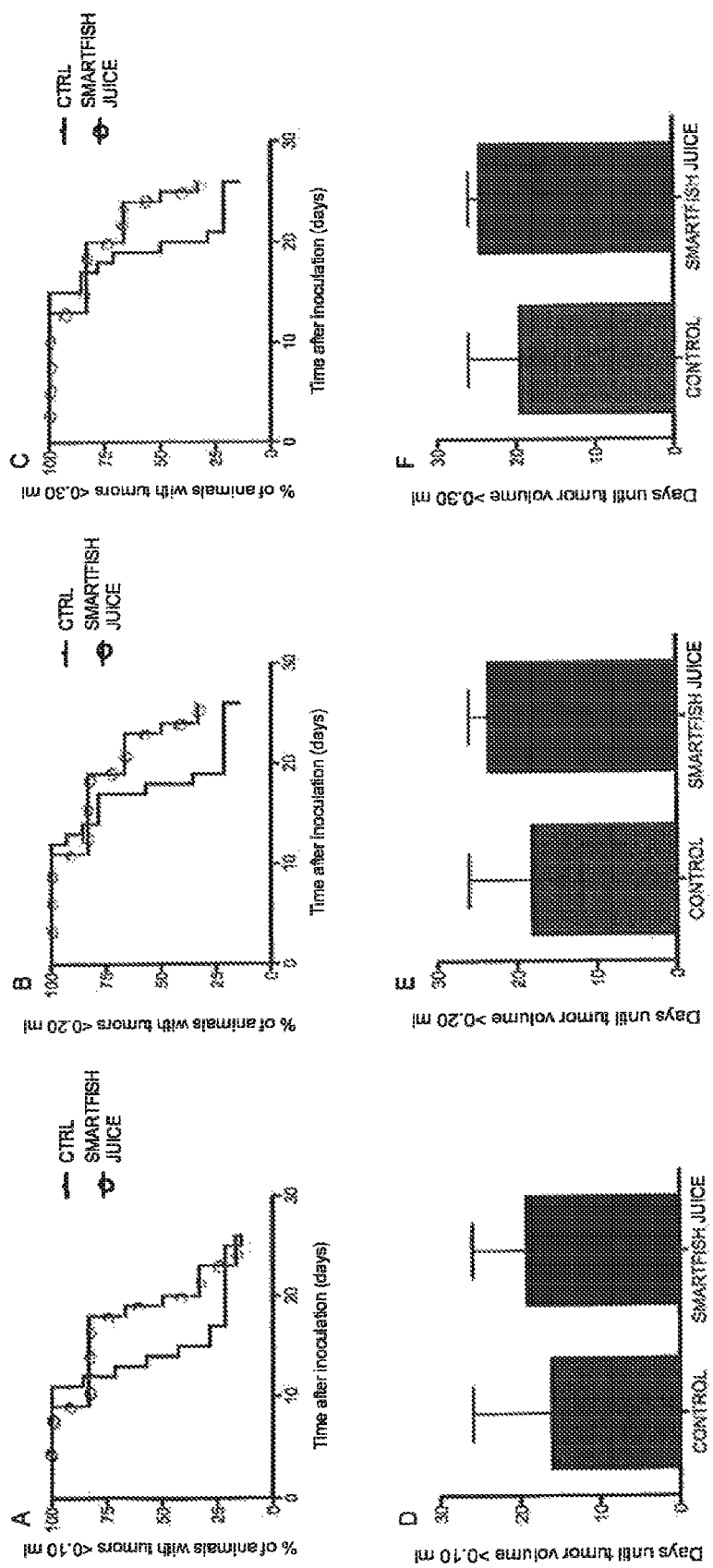
FIG. 4. Illustrates the results of a study wherein nude mice with neuroblastoma xenografts from SK-N-BE(2) were treated with a composition of the invention (Smartfish juice, Nutrifriend 2000) 15 mg/ml (the mice received approximately 45-60 mg EPA-DHA/day/mice) (3 mice, 6 tumors) or drinking water (7 mice, 14 tumors) ad libitum. The graphs display time in days from subcutaneous injection of $10 \times 10^6$ cells, until the tumor exceeds a volume of 0.10 ml (A, D), 0.20 ml (B, E) or 0.30 ml (C, F). In A-C: Kaplan-Meier plots and in D-E: Median time with range; in D: CTRL 14 (11-26) days and SF 19.5 (9-26) days, in E: CTRL 18 (12-26) days and SF 23.5 (11-26) days and F: CTRL 19.5 (15-26) days and SF 24.5 (13-26) days.

In the nude mice study the nude mice with neuroblastoma xenografts from SK-N-BE(2) were treated with the composition (Smartfish juice, Nutrifriend 2000) 15 mg/ml (the mice received approximately 45-60 mg EPA-DHA/day/mice) (3 mice, 6 tumors) or drinking water (7 mice, 14 tumors) ad libitum. The results show a clear delay in tumor development in the mice receiving the composition compared to the control group receiving water (FIG. 4).

Thus, preferred types of cancers that can be treated with the composition of the invention are neurological cancers such as neuroblastoma.

Further preferred types of cancers that can be treated with the composition of the invention are breast cancer, prostate cancer, lung cancer and skin cancer.

Even further examples of types of cancers that can be treated with the composition of the invention are adrenal cancer, anal cancer, bile duct cancer, bladder cancer, bone cancer, brain/CNS tumors, breast cancer, leukaemia, lymphoma, melanoma cancer, osteosarcoma, ovarian cancer, rhabdomysarcoma, soft tissue sarcoma, testicular cancer, thyroid cancer, neuroblastoma, wilms tumor, non Hodkin lymphoma, Hodgkin disease, retinoblastoma, cervical cancer, colon/rectum cancer, esophagus cancer, eye cancer, gallbladder cancer, kidney cancer, laryngeal and hypopharyngeal cancer, liver cancer, lung cancer, lung carcinoid, lymphoma, malignant mesothelioma cancer, multiple myeloma cancer, nasal cancer, cavity and paranasal sinus cancer, nasopharyngeal cancer, oral cavity and oropharyngeal cancer, osteosarcoma, ovarian cancer, pancreatic cancer, penile cancer, pituitary tumors, prostate cancer, retinoblastoma, salivary gland, sarcoma, skin cancer, skin cancer melanoma, skin cancer merkel cell, small intestine cancer, stomach cancer, testicular cancer, thymus thyroid cancer, uterine sarcoma, vaginal cancer, vulgar cancer, and waldenstrom macroglobulinemia.

Also encompassed by the term "treatment of cancer" is amelioration of adverse effects associated with cancer development or ongoing cancer therapy, such as cachexia, vitamin D deficiency, fatigue, stimulation of the immune system etc. are. It may also include treatment of cognitive disorders resulting from the cancer therapy and reduction of relapse.

The post treatment of cancer according to the present invention may be the treatment of any adverse effects associated with the cancer disease per se or the cancer treatment. The post treatment of cancer according to the present invention may be the treatment of cachexia, vitamin D deficiency, fatigue, stimulation of the immune system etc. It may also include treatment of cognitive disorders resulting from the cancer therapy and reduction of relapse.

Nutritional support during treatment and post treatment of cancer is widely used in cancer care. The composition of the present invention serves the purpose of being such a nutritional support, and also in addition being a disease modifying nutrition, and thereby ensures two important dimensions in a cancer treatment regime, all in one single composition.

Such dietary treatment with the composition of the invention might be introduced into classic protocols of human cancer therapy as a new, non-toxic and easily applicable adjuvant cancer therapy without any additional risk to the patient.

In a further preferred embodiment of the present invention the composition may be administered at a dosage in a range from about 600 mg/day to about 5000 mg/day of EPA and DHA, preferably about 3000 mg/day, more preferably about 2000 mg/day and most preferably about 1100 mg/day. In order to achieve therapeutically effect, the dosage may be lower or even higher. The composition may be administered as a drink in a volume range of 50-300 ml, preferably 100 ml, more preferably 200 ml. The person in need of the composition of the invention may drink one or several unit doses of the drink per day. Body weight etc. will be parameters to be used in the dosage calculation; the dosage may therefore vary from one individual to another.

In a preferred embodiment of the present invention the composition may be drinkable, in a capsule or in a powder form.

In a further embodiment the composition of the invention may be used as an adjuvant cancer therapy following surgery, or in combination with other therapeutic agents such as chemotherapeutic agents or anti-inflammatory agents or hormonal drugs or life extension drugs.

The term "in combination" means that the composition of the invention and the other therapeutic agent are administered in such an amount and separated by such administration times as to produce a therapeutic effect. The composition of the invention and the other therapeutic agent may be administered simultaneously or sequential for the use in the treatment and/or post treatment of cancer. The composition of the invention and the other therapeutic agent may be in the form of separate formulations or formulated together in a combined formulation. Included in "other therapeutic agent" is radiotherapy.

Examples of chemotherapeutic agents are: doxorubicin/adriamycin, epirubicin/ellence taxanes such as paclitaxel/taxol and docetaxel/taxotere. Platinum agents such as cisplatin (Platinol, Platinol-AQ) and carboplatin ((Paraplatin), vinorelbine (Navelbine), capecitabine (Xeloda), liposomal doxorubicin (Doxil), gemcitabine (Gemzar), mitoxantrone, ixabepilone (Ixempra®), albumin-bound paclitaxel (Abraxane®), eribulin (Halaven®), cyclophosphamide (Cytoxan, Ceosar), foxorubicin (Adriamycin), etoposide (VePesid), fluorouracil (5-FU), irinotecan (Camptosar), methotrexate (Folex, Mexate, Amethopterin), paclitax topotecan (Hycamtin), Taxol, Oncovin, Vincasar PFS, and vinblastine (Velban).

Examples of anti-inflammatory agents are steroidal anti-inflammatory drugs such as steroids and glucocorticoids. Further examples are non-steroidal anti-inflammatory drug such as ibuprofen, acetylsalisylic acid, celecoxib and other coxib drugs.

Examples of hormonal drugs are LHRH (luteinizing hormone-releasing hormone) agonists such as goserelin, leuprorelin, and triptorelin and LHRH antagonist such as degarelix. Further examples are steroidal anti-androgens such as cyproterone acetate and non-steroidal anti-androgener such as bicalutamide, nilutamide, and flutamide.

Examples of life extension drugs are anti-diabetic drugs such as metformin, statins, acetylsalicyclic acid, tadalafil and DHEA (dehydroepiandrosterone).

The amount of the additional therapeutic agent, when administered in combination with the composition of the invention, is substantially the amount and dosage regimen usually employed by the clinician in therapy. At any rate, the clinician may vary the amount of the additional drug (or mixture of additional drugs) based on the patient's clinical picture.

From the above, it may be concluded that use of the composition according to the present invention shows clear effects in inhibiting cell proliferation, increasing apoptosis and delaying tumor development, thus is suitable in cancer treatment.

The invention will now be further illustrated with reference to the following non-limiting examples.

EXAMPLES

Example 1

Three human epithelial colon cancer cell lines were used. Caco-2 grown in DMEM containing 20% FCS, 1% of nonessential amino acids, 100 U/mL penicillin, and 100 µg/mL streptomycin. HT-29 and HCT116 grown in DMEM containing 10% FCS, 1% of nonessential amino acids, 100 U/mL penicillin, and 100 µg/mL streptomycin. DMEM containing 10% FCS, 1% of nonessential amino acids, 100 U/mL penicillin, and 100 µg/mL streptomycin (cell medium) was used for all cell lines in all experiments.

Samples:
1. The composition of the present invention (Nutrifriend 1100) containing fruit juice (from apple, pear, pomegranate, aronia, passionfruit), fish oil (7 mg/ml), protein isolate from milk, pectin, aroma from jackfruit, rosemary extract, vitamin E, vitamin D and soya lecithin.
2. Good (nonoxidized) fish oil from salmon, PV 3 and AV 2 (7 mg/ml in a FCS and DMSO emulsion)
3. Oxidized fish oil from salmon, PV 15 and AV 13 (7 mg/ml in a FCS and DMSO emulsion)

The fish oils were prepared as an emulsion in the same concentration as the fish oil used in the composition of the invention (Nutrifriend 1100) before addition to the cells as follows: 7 mg oil were mixed with 10 γ1 DMSO, vortexed and sonicated for 10 sec at 40 V on ice. Then 1 ml FCS was added and the mixture was vortexed and sonicated for 10 sec at 40 V on ice.

Treatment of Cells and Measurements of Antiproliferative Effects

The composition of the invention (Nutrifriend 1100) and the two oil emulsions were diluted in cell medium to the final concentrations (with regard to oil content) as shown in Table 1.

TABLE 1

| Dilution of samples | | | |
| --- | --- | --- | --- |
| Oil conc. | Vol sample (γl) | Vol medium (γl) | Total vol (γl) |
| 0.35 mg/ml | 50 | 950 | 1000 |
| 0.7 mg/ml | 100 | 900 | 1000 |
| 1.4 mg/ml | 200 | 800 | 1000 |
| 2.1 mg/ml | 300 | 700 | 1000 |

Cells were seeded in 96 well plates with 100 µl medium 24 hours before the experiment. At the start of the experiment, the growth medium was removed and replaced with cell medium containing the indicated samples. Cells were then incubated for either 4 hours for measurements of apoptosis or 24 hours for measurements of cell proliferation.

Cell proliferation was measured using the MTT assay. After 24 hours incubation with samples the cells were washed once with PBS to remove traces of samples, supplied with new cell medium (100 µL/well) and then treated with MTT standard solution (15 µL/well) at 37° C. for 2 h. The cell proliferation rate was determined by the ability of the metabolic active cells to cleave tetrazolium sodium salt to purple formazan crystals. The MTT containing medium was removed and the cellular purple precipitate was dissolved in 0.04 M HCl in 2-propanol (100 μL/well). The absorbance was measured at 562 nm by a SPECTROstar Nano plate reader (BMG Labtech Gmbh, Germany). Every sample was measured in three replicates in each experiment, and the experiments were repeated three times.

In addition, the Caco-2 cell line was analyzed for apoptosis using the Caspase-Glo® 3/7 Assay (Promega, Madison, Wis.). This assay is a homogenous, luminescent assay that measures caspase-3 and -7 activities that occur during apoptosis. A shorter incubation time is used as the activities of caspase-3 and -7 increases in the initial phase of apoptosis. After 4 hours incubation with samples the cells were washed once with PBS to remove traces of samples, supplied with new cell medium (100 μL/well) and then treated with luminogenic caspase 3/7 substrate (100 μL/well) at room temperature for 1 h. The caspase 3/7 substrate is cleaved by cellular caspase-3/7, and a substrate for luciferase (aminoluciferin) is released resulting in luciferase reaction and the production of light. Luminescence was detected using a Glomax96 Microplate Luminometer (Promega, Madison, Wis.).

The results indicate that the composition of the present invention, have an antiproliferative effect on all three cell lines (FIG. 1), and that this inhibition of cell proliferation is due to an induction of apoptosis (FIG. 2). The largest effect was seen on the HCT116 cell line, were a concentration of 0.7 mg/ml (with respect to oil content) gave a significant (about 50%) decrease in cell proliferation compared to control cells. Interesting and as evident from FIG. 3, the two fish oil control samples gave no inhibition of cell proliferation.

Example 2

Mice with SK-N-BE(2) Xenograft Tumors Treated with the Composition (Smartfish Juice)

Nude mice with neuroblasoma xenografts were treated with the composition of the present invention (Smartfish juice, Nutrifriend 2000) with a dosage of 15 mg/ml (the mice received approximately 45-60 mg EPA-DHA/day/mice) (3 mice, 6 tumors) or drinking water (7 mice, 14 tumours) ad libitum. As can be seen from FIG. 4 mice receiving the composition showed delay in tumor development compared to the control group.

Example 3

Weight Gain in a Breast Cancer Patient when Using the Composition of the Present Invention A breast cancer patient (with relapse) had a body weight of 47 kg and a very low to vitamin D value. The patient was introduced to the composition of the present invention (Nutrifriend 1100) and started to take two doses per day (each dose (200 ml) comprises 1100 mg EPA/DHA). After two weeks she experienced weight gain and increase in appetite. The patient continued to gain weight and had reached 54 kilo after a few weeks. In addition she felt that her strength and vitality had recurred.

Example 4

Measurement of Apoptosis by Caspase-3 in Co-Culture of Pancreatic Cancer Cells and NK-Cells Patients with pancreatic cancer have poor prognosis attributed to high potential for metastatic spread, protection by dense mesenchymal and inflammatory cell environment, and immune suppression with deactivation of natural killer (NK) cells by tumor cells. Curcumin has been tested in a previous clinical trial with modest results. In the following study, a composition of the invention with or without addition of curcumin has been tested with respect to their potential of stimulating pancreatic cancer cell killing by NK cells.

Methods:

Cell Culture:

Mia Paca2 (MP2) and L3.6 cells from pancreatic ductal adenocarcinoma so (PDAC) were obtained from T. Donahue, UCLA Surgery and were propagated in Dulbecco's Modified Eagle's Medium (DME) with 10% foetal calf serum. 10,000 cells were plated in each well of 24-well plates and were grown at 37° C. and 24 h to near confluence before testing.

Nk Cells:

These were isolated from human blood by NK cell isolation kit (Stem cell technologies, Vancouver, Canada). NK cells were activated by treatment with IL-2 or IL2/CD16 as described in Tseng, H. C. et al. "Increased lysis of stem cells but not their differentiated cells by natural killer cells; de-differentiation or reprogramming activates NK cells." PLOS One 5(7): e11590, 2010.

Composition of the Invention—Smartfish Nutrifriend 2000.

Composition of the invention (Nutrifriend 2000) containing DHA (1000 mg/200 ml) and EPA (1000 mg/200 ml) was purchased by the company Smartfish AS, Oslo, For use in cell culture, diluted 1:2 with fetal calf serum, sonicated for 30 sec and then diluted 1:100 in DMEM with 10% fetal calf serum.

Cytocidal Assay; Co-Culture of MP2 or L3.6 Cells with NK Cells:

NK cells were added to MP2 or L3.6 cells at a ratio of 5 NK cells per 1 MP2 cell. The co-cultures were treated with Smartfish. Addition of DHA (50 nM) or resolvin D1 (RvD1 from Cayman Chemical company, Ann Arbor, Mich., 50 nM) were tested as controls. The co-cultures is were grown for 48 hours, harvested and tested by the caspase-3 assay.

Caspase-3 Assays:

The enzymatic caspase-3 assay was performed by the CaspACE-3 assay G-7351 (Promega Corporation, Madison, Wis.) according to the manufacturer's instructions.

Caspase-3 Immunofluorescent Microscopic Assay:

MP2 cells were grown to partial confluence in 8-well chamber slides (Corning) in DME with 10% fetal calf serum and were treated 24 hours as stated. Then they were fixed by 4% paraformaldehyde, permeabilized using 0.25 Triton, stained using the indirect technique with rabbit anti-caspase-3 (active) (Genetex) at 1:200 dilutions followed by ALEXA-fluor-donkey anti-rabbit 568 (In Vitrogen) at 1:200 dilutions and FITC-phalloidin (Sigma) at 1:500 dilution, mounted using Prolong Gold antifade with DAPI (In Vitrogen).

Statistical Analysis:

The data were analyzed by comparing the range of means (mean+/−2× standard error of mean). When indicated the exact value was calculated by the Fisher exact test.

Results:

Enzymatic Caspase-3 Assay

Table 1 shows the results of treatment of co-culture of pancreatic cancer cells (MP2 cells) and NK cells with Smartfish. The addition of DHA and RvD1 are shown as controls.

TABLE 1

| | | | | | | |
|---|---|---|---|---|---|---|
| MP2 cells | X | | X | X | X | X |
| NK (IL-2) | | X | X | X | X | X |
| RvD1 | | | | X | | |
| DHA | | | | | | X |

TABLE 1-continued

| | | | | | | |
|---|---|---|---|---|---|---|
| Smartfish | | | | | | X |
| Casp-3 (uM) X₁ | 3.8 | 2.1 | 6 | 6 | 5.7 | 11 |
| X₂ | 3.5 | 2.1 | 5.4 | 6.3 | 6.6 | 9.1 |
| X₃ | 4.1 | 2.4 | 5.2 | 6.6 | 6 | 9.1 |
| Mean | 3.8 | 2.2 | 5.5 | 6.3 | 6.1 | 9.6 |
| Mean ± 2 × S.D./ Sqrt N | 3.8 ± 0.31 | 2.2 ± 0.18 | 5.5 ± 0.48 | 6.3 ± 0.31 | 6.1 ± 0.48 | 9.6 ± 1.10 |
| 95% range | (3.49–4.11) | (2.02–2.38) | (5.02–5.98) | (5.99–6.61) | (5.62–6.58) | (8.5–10.7) |

As shown in Table 1, MP2 cells alone and IL-2 stimulated NK cells alone, showed very low caspase-3 expression (3.8 μM and 2.2 μM, respectively), whereas in the co-culture of MP2 cells with NK cells the caspase-3 expression was higher (5.5+/−0.48 μM), and was slightly increased by the addition of RvD1 (6.3+/−0.31 μM) or DHA (6.1 μM+/−0.48 μM). The treatment of the co-culture of cancer with NK cells by Smartfish increased apoptosis expression significantly (9.6+/−1.1 μM).

Thus, it has been shown that Smartfish potentiate cytocidal effects of NK cells on cancer cells. Smartfish potentiate the apoptosis of pancreatic cancer cells by NK cells.

Results;

Caspase-3 Immunofluorescent Microscopic Assay

The experimental set up was as outlined in FIG. 6. Briefly, NK cells were stimulated with IL-2 or a combination of IL-2 and CD16. Unstimulated NK cells served as control cells. The two groups of stimulated NK cells were co-cultured with the pancreatic cancer cells line L3.6. Control NK cells and the co-cultures were further stimulated with Smartfish.

Immunofluorescence:

The co-cultures of L3.6 cancer cells (pancreatic ductal adenocarcinoma (PDAC) cancer cells) with NK cell were fixed in phosphate buffered salt solution (PBS) containing 4% paraformaldehyde (PFA), permeabilized by 0.25 Triton X-100 (Sigma)/PBS, stained 30 min with a predetermined dilution of the primary antibody anti-active Caspase 3 (rabbit anti-human IgG GTX22302, GeneTex) at 1:200 dilutions, 30 min with the secondary antibody fluorescent donkey anti-rabbit antibody (Alexa Fluor 568, Invitrogen) (1:200 dilution), 20 min by 1:500 dilution of fluorescent Phalloidin (488, Sigma), and mounted in the aqueous mounting medium with DAPI (Prolong Gold antifade; Life Technologies). Pictures were taken by fluorescence microscope (Olympus) at 20× and/or 40×.

The results are set forth in FIG. 6 showing induction of apoptosis (caspase-3-positive=red) in cultures of L3.6 immortalized pancreatic adenocarcinoma cells (=large green cells) co-cultured overnight with NK (IL-2) or NK (IL-2/CD16) cells (=small green or shriveled cells) in an immunofluorescence assay.

NK cells cultured alone showed a shriveled appearance, whereas NK cells cultured with Smartfish showed a normal green cytoplasma indicating protection by Smartfish (Panel A and D of FIG. 6).

Co-culture of NK cells (IL-2 stimulated) and L3.6 cancer cells without or with Smartfish stimulation showed the following: L3.6 cancer cells have mostly green cytoplasm indicating that they are surviving, whereas the co-culture stimulated with Smartfish showed that only few cancer cells are surviving and displaying yellow or orange cytoplasm indicating their apoptosis (Panel B and F of FIG. 6).

Co-culture of NK cells (IL2 and CD16 stimulated) and L3.6 cells without or with Smartfish showed the following: L3.6 cancer cells have mostly green cytoplasm indicating that they are surviving, whereas the co-culture stimulated with Smartfish showed that the cancer cells are in a clump displaying apoptosis (yellow or red). (Panel (C) and (E) of FIG. 6)

NK cells in the co-cultures (panel (B), (C), (E), (F) of FIG. 6) are apoptotic, i.e. showing either only nuclei or red cytoplasm. Thus cancer cells and NK cells both die in the fight but more cancer cells die in presence of a composition of the invention. Thus, it has been shown that a composition of the invention potentiate the cytocidal effects of NK cells on cancer cells, thus increases the apoptosis.

Induction of Interferon-γ

The effect on production of interferon-γ (INFγ) by NK cells was studied. Experimental conditions were as outlined above. IFNγ was measured by using a commercially available IFNγ assay.

The IFNγ assay showed that IFNγ was not at all produced by INK cells alone but was produced by INK cells in co-culture with MP2 cells at a level of 158 pg/ml. The production of interferon-γ was decreased by Smartfish to 119 pg/ml. The results are set forth in table 2 below.

TABLE 2

| | | | | |
|---|---|---|---|---|
| MP2 cells | X | | X | X |
| NK (IL-2) | | X | X | X |
| Smartfish | | | | X |
| IFNγ (pg/ml) | 0 | 0 | 158 | 119 |

Thus, it has been shown that the composition of the invention is able to reduce the production of IFNγ.

Having now described the present invention in some detail by way of illustration and example for purpose of clarity of understanding, it will be obvious to one of ordinary skill in the art that same can be performed by modifying or changing the invention by using a wide and equivalent range of conditions and other parameters thereof, and that such modifications or changes are intended to be encompassed within the scope of the appended claims.

I claim:

1. A method for treatment and/or post treatment of cancer in a subject in need of treatment thereof, the method comprising administering to the subject a therapeutically effective amount of a composition comprising:
   a combination of fish oil, and
   juice in an oil-in water emulsion,
   wherein the fish oil has a totox value below 20 and an omega-3 content above 10% by weight based on the total weight of the fish oil and wherein a suitable emulsifier is used to stabilize the emulsion,
   wherein the cancer is selected from the group consisting of prostate cancer, lung cancer, and skin cancer and the post treatment of cancer comprises treatment of cachexia, vitamin D deficiency, fatigue, or stimulation of the immune system, and
   wherein said suitable emulsifier is selected from the following group consisting of milk solids, whey protein, oat protein, and pea protein.

2. The method of claim 1, further comprising administering a therapeutic agent for the treatment and/or post treatment of cancer in combination with the composition.

3. The method according to claim 1, wherein the totox value of the fish oil is below 10.

4. The method according to claim 1, wherein the fish oil content is about 0.5 to 15% by weight based on the total weight of the composition.

5. The method according to claim 1, wherein the content of the juice is about 30-95% by weight based on the total weight of the composition.

6. The method according to claim 1, wherein the juice is from a fruit or a berry having a suitable high level of antioxidants.

7. The method according to claim 6, wherein the juice is from a fruit or a berry selected from the group consisting of pomegranate, apricot, grapefruit, orange, cranberry, rosehip, pineapple, black chokeberry, mulberry, cloudberry, acerola, raspberry, watermelon, peach, grapes, cherry, jambolao, apple, mango, pear, aronia, passionfruit and kiwi.

8. The method according to claim 6, wherein the juice is selected from the group consisting of beetroot, carrot, lingonberry (cowberry), guava, blackberry and greens.

9. The method according to claim 1, wherein the composition further comprises pectin.

10. The method according to claim 1, wherein the composition further comprises a sweetener, a flavoring agent, an antioxidant and a preservative.

11. The method according to claim 1, wherein the composition is administered at a dosage in a range from about 600 mg/day to about 5000 mg/day of EPA.

12. The method according to claim 1, wherein the composition is drinkable, or in a capsule or powder form.

13. The method according to claim 1, wherein the composition is administered at a dosage in a range from about 600 mg/day to about 3000 mg/day of EPA and DHA.

14. The method according to claim 1, wherein the composition is administered at a dosage in a range from about 600 mg/day to about 2000 mg/day of EPA and DHA.

15. The method according to claim 1, wherein the composition is administered at a dosage in a range from about 600 mg/day to about 1100 mg/day of EPA and DHA.

* * * * *